United States Patent
Lehnherr et al.

(10) Patent No.: US 12,274,722 B1
(45) Date of Patent: Apr. 15, 2025

(54) ANTIBIOTIC FREE TREATMENT OF MASTITIS

(71) Applicant: PHAGE TECHNOLOGY CENTER GMBH, Boenen (DE)

(72) Inventors: Hansjörg Lehnherr, Bern (CH); Tatiana Lehnherr-Ilina, Hamm (DE); Michael Fink, Hamm-Rhynern (DE)

(73) Assignee: PHAGE TECHNOLOGY CENTER GMBH, Boenen (DE)

( * ) Notice: Subject to any disclaimer, the term of this patent is extended or adjusted under 35 U.S.C. 154(b) by 0 days.

(21) Appl. No.: 18/644,438

(22) Filed: Apr. 24, 2024

(51) Int. Cl.
*A61K 35/76* (2015.01)
*A01N 63/40* (2020.01)
*A01P 1/00* (2006.01)
*A61P 31/04* (2006.01)
*C12N 7/00* (2006.01)

(52) U.S. Cl.
CPC .............. *A61K 35/76* (2013.01); *A01N 63/40* (2020.01); *A01P 1/00* (2021.08); *A61P 31/04* (2018.01); *C12N 7/00* (2013.01)

(58) Field of Classification Search
None
See application file for complete search history.

(56) References Cited

U.S. PATENT DOCUMENTS

| | | |
|---|---|---|
| 8,377,431 B2 | 2/2013 | Yoon et al. |
| 11,311,582 B2 | 4/2022 | Paros et al. |
| 2018/0273910 A1* | 9/2018 | Rohwer ............... A61P 31/04 |
| 2018/0333444 A1* | 11/2018 | Paros .................. A61P 31/04 |
| 2019/0307818 A1 | 10/2019 | Bassler et al. |

FOREIGN PATENT DOCUMENTS

IN 202041006569 * 8/2021

OTHER PUBLICATIONS

Recognized Budapest Treaty International Depository list, accessed Sep. 5, 2024.*
Leibniz-Institut DSMZ History timeline, accessed Sep. 5, 2024.*
Poudel et al. (Matrix Science Pharma. Jul. 1, 2021;5(3):49-53).*
Gill, J. J., J. C. Pacan, M. E. Carson, K. E. Leslie, M. W. Griffiths, and P. M. Sabour. 2006. "Efficacy and Pharmacokinetics of Bacteriophage Therapy in Treatment of Subclinical *Staphylococcus aureus* Mastitis in Lactating Dairy Cattle." Antimicrobial Agents and Chemotherapy 50 (9): 2912-18. https://doi.org/10.1128/AAC.01630-05.
Manrique, Pilar, Michael Dills, and Mark J. Young. 2017. "The Human Gut Phage Community and Its Implications for Health and Disease." Viruses 9 (6): 9-11. https://doi.org/10.3390/v9060141.
Nale, Janet Y., and Neil R. McEwan. 2023. "Bacteriophage Therapy to Control Bovine Mastitis: A Review." Antibiotics 12 (8): 1-21. https://doi.org/10.3390/antibiotics12081307.
Ngassam-Tchamba, C., J. N. Duprez, M. Fergestad, A. De Visscher, T. L'Abee-Lund, S. De Vliegher, Y. Wasteson, et al. 2020. "In Vitro and in Vivo Assessment of Phage Therapy against *Staphylococcus aureus* Causing Bovine Mastitis." Journal of Global Antimicrobial Resistance 22: 762-70. https://doi.org/10.1016/j.jgar.2020.06.020.
O'Flaherty, S., R. P. Ross, J. Flynn, W. J. Meaney, G. F. Fitzgerald, and Aidan Coffey. 2005. "Isolation and Characterization of Two Anti-Staphylococcal Bacteriophages Specific for Pathogenic *Staphylococcus aureus* Associated with Bovine Infections." Letters in Applied Microbiology 41 (6): 482-86. https://doi.org/10.1111/j.1472-765X.2005.01781.x.
Isabel Titze et al. "Ecacy of Bacteriophages Against *Staphylococcus aureus* Isolates from Bovine Mastitis", Feb. 26, 2020, 22 pages.

* cited by examiner

*Primary Examiner* — Shanon A. Foley
(74) *Attorney, Agent, or Firm* — Raj S. Davé; Davé Law Group, LLC (57) ABSTRACT

Embodiments relate to a composition comprising a bacteriophage or a mutant thereof and a storage solution, wherein the bacteriophage or the mutant thereof is capable of killing a Gram-positive bacterium comprising *Staphylococcus aureus*, wherein the composition is stable for at least about a year at 39.2-46.4° F. (4-8° C.).

20 Claims, 4 Drawing Sheets

ANTIBIOTIC FREE TREATMENT OF MASTITIS

FIELD OF THE INVENTION

This invention relates to a composition to treat mastitis and the process thereof. In particular, the invention relates to bacteriophage compositions to treat mastitis.

BACKGROUND OF INVENTION

Mastitis is an inflammation of the breast or udder, usually associated with breastfeeding or milking. Symptoms typically include local pain and redness. There is often an associated fever and general soreness.

Mastitis typically develops when milk is not properly removed from the breast or udder. Milk stasis can lead to blocking of milk ducts in the breasts, leading to infection.

Bovine mastitis is one of the most common diseases in dairy cows worldwide. Mastitis reduces milk yield and increases milk production costs due to discarded milk, preventative and therapeutic expenses, and premature culling (Halasa et al. Vet. Q. (2007) 29: 18-31; Heikkila et al. J. Dairy Sci. (2012) 95: 139-150). Additionally, mastitis has a significant negative impact on milk quality and animal welfare (Bradley, A. J. Vet. J. (2002) 164: 116-128).

Infectious pathogens commonly associated with mastitis are *Staphylococcus aureus, Streptococcus* spp., Gram-negative bacilli such as *Escherichia coli* and *Salmonella* spp., and mycobacteria. Fungi such as *Candida* and *Cryptococcus* have also been identified in rare instances.

Previously, bacterial mastitis has been treated with various ß-lactam antibiotics, marbofloxacin, kanamycin, tetracycline, clindamycin and erythromycin, or an antifungal agent such as fluconazole in cases of fungal infection.

However, since 1980s, excessive use of antibiotics has generated many antibiotic resistant strains and since the year 2000, multidrug-resistant strains have been frequently reported. Vestergaard M. et al. states, "*Staphylococcus aureus* is capable of becoming resistant to all classes of antibiotics clinically available and resistance can develop through de novo mutations in chromosomal genes or through acquisition of horizontally transferred resistance determinants." (ASM Journals; Microbiology Spectrum; Vol. 7, No. 2.)

Further, use of antibiotics leads to deposition of antibiotic residue in the person consuming milk or milk derived product. For example: Sachi S et al., in the article titled, 'Antibiotic residues in milk: Past, present, and future.' J Adv Vet Anim Res. 2019 Jul. 11; 6(3):315-332. doi: 10.5455/javar.2019.f350. PMID: 31583228; PMCID: PMC6760505 state, "administered parent antibiotics or their metabolites become deposited in animal tissues and matrix intended to be used for human consumption, where the concentration is beyond the permitted level for a certain period of time, known as antibiotics residues [10]. Among the vital causes of presence of antibiotic residues in milk, dry cow therapy and usage in mastitis treatment are of great importance [11] The developing countries are in greater risk due to residues in milk than the developed ones. Poor detection facilities as well as lack of proper monitoring system of residues in foods considering the maximum residue limits (MRLs) might be taken as vital causes for higher risk of milk derived antibiotic residues [12]."

In another article Rajala-Schultz et al. titled, 'Prudent Use of Antibiotics in Dairy Cows: The Nordic Approach to Udder Health' *Front. Vet. Sci.,* 5 Mar. 2021 Sec. state, "In a time when antibiotic resistance is recognized as a threat to animal and human health (3), food animal producers and veterinarians must continue to strive for prudent antibiotic use and sustainable production. This is an obvious One Health challenge and all stakeholders, industry in the front row, must actively participate. If consumers do not find animal-derived food sustainably and ethically produced, demand and markets for these products will likely shrink. In fact, market demands and consumer concerns e.g., on animal welfare and antibiotic resistance can be driving forces for changes in routines and procedures used in animal production (40, 41)."

The new approach drawing our attention to is to use bacteriophage. The term bacteriophage means 'eating bacteria'. Bacteriophages (phages) are natural bacterial viruses that specifically infect and kill bacterial cells. They are omnipresent in our environment and are harmless for humans, animals and plants. Indeed, the highest concentrations of bacteriophages in nature are found in our digestive tract (Manrique, Dills, and Young 2017), where the bacteriophages play an important role in our digestion.

A bacteriophage needs a host for its survival and every bacterium has its specific bacteriophages. A bacteriophage invades a host and is multiplicated therein. Then, the bacteriophage expresses a group of enzymes necessary for decomposing the cell wall of the host bacterium.

The specificity of bacteriophages allows them to act directly against pathogenic bacteria. In contrast, antibiotic treatment carries collateral damage, disrupting the microbiome. Phage therapy offers no off-target effects, preventing effects from microbiome disturbances such as antibiotic-associated diarrhoea, mucosal candidiasis, pseudo-membranous colitis and even long-term metabolic and immunological disorders.

Wild type *Staphylococcus aureus* strains often carry defense mechanisms, such as restriction/modification systems, that render them less susceptible to bacteriophage infection.

Bacteriophages have previously been considered to treat mastitis, but no existing bacteriophage product is an efficient, natural and sustainable treatment of bovine mastitis.

SUMMARY OF INVENTION

Wild type *Staphylococcus aureus* strains often carry defense mechanisms, such as restriction/modification systems, that render them less susceptible to bacteriophage infection.

In an embodiment, present invention provides a composition having one or more bacteriophages that overcome the bacterial defense mechanisms.

In an embodiment, present invention provides an efficient, natural, and sustainable treatment of bovine mastitis caused by *Staphylococcus aureus*.

In an embodiment, present invention provides a composition having one or more bacteriophages that overcome the bacterial defense mechanisms.

Embodiments of the present invention have also successfully transferred the laboratory results to a veterinary application.

An embodiment relates to a composition comprising a bacteriophage or a mutant thereof and a storage solution, wherein the bacteriophage or the mutant thereof is capable of killing *Staphylococcus aureus*, wherein the composition is stable for at least about a year at 39.2-46.4° F. (4-8° C.).

In an embodiment, the storage solution comprises an isotonic solution comprising a salt of sodium and either or both calcium and magnesium.

In an embodiment, the composition is substantially freely miscible with raw milk.

In an embodiment, the composition is a medical cleaner.

In an embodiment, wherein the bacteriophage or the mutant thereof is selected from bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022.

In an embodiment, the composition comprises at least two bacteriophages selected from the group consisting of EB1.11, EB1.25, EB1.27, MA2.74 and STA1.29.

In an embodiment, the composition comprises at least three bacteriophages selected from the group consisting of EB1.11, EB1.25, EB1.27, MA2.74 and STA1.29.

In an embodiment, the composition comprises at least four bacteriophages selected from the group consisting of EB1.11, EB1.25, EB1.27, MA2.74 and STA1.29.

In an embodiment, bacteriophages comprise EB1.11, EB1.25, EB1.27, MA2.74 and STA1.29.

In an embodiment, the composition does not lead to coagulation of raw milk.

In an embodiment, the composition does not contain a phosphate buffer.

In an embodiment, the composition does not contain a TRIS buffer.

In an embodiment, the composition is configured to target a Gram-positive bacterium.

In an embodiment, the Gram-positive bacterium comprises *Staphylococcus aureus* spps.

In an embodiment, the composition further contains a pharmaceutical acceptable excipient.

In an embodiment, the composition is configured to treat mastitis in a mammal.

In an embodiment, the composition is configured to treat bovine mastitis.

In an embodiment, mastitis is chronic mastitis.

In an embodiment, mastitis is subclinical mastitis.

In an embodiment, the composition has a concentration of $1 \times 10^9$ PFU/mL per bacteriophage.

In an embodiment, the bacteriophage or the mutant thereof is selected from bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022.

In an embodiment, the composition is stable for about 2 years.

In one embodiment, the composition is stable for about 3 years.

In an embodiment, the bacteriophage concentration reduces to less than 0.5 log in a composition during a storage period. In an embodiment, the composition potency is in a range of about $1 \times 10^7$ PFU/mL to about $1 \times 10^{10}$ PFU/mL per bacteriophage.

In an embodiment, the composition has a pH in the range of about 6 to 8.

In an embodiment, the bacteriophage or the mutant thereof is configured to overcome a bacterial defense mechanism.

In an embodiment, the bacteriophage or the mutant thereof is epigenetically modified by the host bacterium.

In an embodiment, the host bacterium is *Staphylococcus aureus*.

In an embodiment, the bacteriophage or the mutant thereof is epigenetically modified by a host bacterium.

In an embodiment, composition comprising a mixture of at least two bacteriophage strains, wherein the bacteriophage strains are selected from bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022.

In an embodiment, the composition is administered to a mammal in a dosage range between about $1 \times 10^7$ to about $1 \times 10^{10}$ PFU/ml of each phage at least once daily.

In an embodiment, the composition further comprises an antibiotic.

In an embodiment, the isotonic solution comprises a sodium salt with calcium and/or magnesium salt.

In an embodiment, the sodium salt comprises sodium chloride.

In an embodiment, the isotonic solution comprises a calcium salt and a magnesium salt.

In an embodiment, magnesium salt has a higher concentration than calcium salt.

In an embodiment, magnesium salt is about 8 to 12 times more in concentration compared to calcium salt.

In an embodiment, the sodium salt is about 0.9 w/v % in the isotonic solution.

In an embodiment, a kit comprising a composition and instruction of use of the same. The kit further comprises an isotonic solution to dilute the composition.

An embodiment, composition comprising a strain of a bacteriophage or a mutant thereof, wherein the strain is selected from bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022, wherein the composition further comprises a storage solution comprising an isotonic solution, wherein the composition is stable for at least about a year at 39.2-46.4° F. (4-8° C.) and pH 6-8.

In an embodiment, a method of treating or preventing a disease caused by a bacterial infection in a mammal comprising administering to the mammal an effective amount of a composition comprising a purified bacteriophage strain, wherein the bacteriophage strain is selected from bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022. The depository is the Leibniz Institute DSMZ-German Collection of Microorganisms and Cell Cultures, located at Inhoffenstraße 7B, 38124 Braunschweig, Science Campus Braunschweig-Sud, GERMANY.

In an embodiment, the composition is administered intra mammary via teat channel.

In one embodiment, the disease comprises mastitis.

In an embodiment, mastitis comprises bovine mastitis.

In an embodiment, the *staphylococcus* spp. comprises *Staphylococcus aureus*.

In an embodiment, the composition is administered to a lactating mammal after milking the mammal.

In an embodiment, the composition is administered via a teat channel.

In one embodiment, the lactating mammal comprises a bovine animal.

In an embodiment, the bovine animal comprises a cow.

In an embodiment, the composition is administered via a teat channel into udder of the lactating mammal.

In an embodiment, the composition further comprises an isotonic solution.

In an embodiment, the composition administered into the lactating mammal is miscible with raw milk of the mammal.

In an embodiment, the composition administered into a bovine avoids coagulation of the raw milk in a bovine udder and teats.

In an embodiment, the composition is administered intra-mammarily.

In an embodiment, the composition is administered during a dry period.

In an embodiment, a composition comprising: 1) a first bacteriophage with a podovirus morphology, 2) a second bacteriophage with a myovirus morphology, 3) a storage solution comprising salt of sodium with magnesium and/or calcium salt, wherein the composition is stable for about a year at room temperature.

In an embodiment, the magnesium salt comprises magnesium chloride.

In an embodiment, the calcium salt comprises calcium chloride.

In an embodiment, the first bacteriophage is selected from bacteriophage strain EB1.11 deposited under number DSM 34393, bacteriophage strain EB1.25 deposited under number DSM 34394, bacteriophage strain EB1.27 deposited under number 34395, wherein said strains were deposited at German Collection of Microorganisms on Sep. 28, 2022. In an embodiment, wherein the second bacteriophage is selected from bacteriophage strain STA1.29 deposited under number DSM 34396 and bacteriophage strain MA2.74 deposited under number DSM 34397, wherein said strains were deposited at German Collection of Microorganisms on Sep. 28, 2022.

BRIEF DESCRIPTION OF THE FIGURES

The accompanying drawings, which are included to provide further understanding of the present invention disclosed in the present disclosure and are incorporated in and constitute a part of this specification, illustrate aspects of the present invention and, together with the description, serve to explain the principles of the present invention. In the drawings.

DETAILED DESCRIPTION

Definitions and General Techniques

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one", or similar language, is used. Also, as used herein, the terms "has," "have," "having," or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately", "substantially" or "about" can, in some embodiments, mean within plus or minus ten percent of the stated value. In other embodiments, "approximately" "substantially" or "about" can mean within plus or minus five percent of the stated value. In further embodiments, "approximately" "substantially" or "about" can mean within plus or minus three percent of the stated value. In yet other embodiments, "approximately" "substantially" or "about" can mean within plus or minus one percent of the stated value.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures, procedures, and techniques of embodiments herein, and other related fields described herein, are those well-known and commonly used in the art.

The recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications, without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For the purpose of clarity, details relating to technical material that are known in the technical fields related to the invention have not been described in detail so as not to unnecessarily obscure the present invention.

The following terms and phrases, unless otherwise indicated, shall be understood to have the following meanings.

As used herein, the term "bacteriophage" and "phage" are used interchangeably to refer to a bacteriophage isolate in which members of the isolate have substantially the same genetic makeup, such as sharing at least about any of 99%, 99.9% or more sequence identity in the genome. "Bacteriophage" or "phage" refers to the parent bacteriophage as well as the progeny or derivatives (such as genetically engineered versions) thereof. The bacteriophage can be a naturally occurring phage isolate, or an engineered phage, including vectors, or nucleic acids that encode at least all essential genes, or the full genome of a phage to carry out the life cycle of the phage inside a host bacterium.

As used herein, the term, "mutant" refers to an altered or reduced or modified bacteriophage sequence such that the mutant is still able to target a host bacterium. In an embodiment, a mutant has more than any of 96% degree such as 97%, 98% of identity with its parent sequence.

As used herein, the term "bacterium" refers to a bacterial isolate in which members of the isolate have substantially the same genetic makeup, such as sharing at least about any of 99%, 99.9% or more sequence identity in their genome. "Bacterium" may refer to the same bacterium genus, species, strain, or clone. "Bacterium" refers to the parent bacterium as well as the progeny or derivatives (such as genetically engineered versions) thereof.

As used herein, the term "host" refers to the bacteria that can be targeted by the bacteriophage.

As used herein, the term "mastitis" refers to an inflammation of a mammary gland. In dairy cattle, the mammary gland is commonly referred to as "udder". Mastitis can be caused by a physical injury, introduction of chemicals, viruses, fungus, parasites or, most commonly, bacterial invasion and host reactions to their toxins. "Mastitis" can be used to describe all forms of such inflammation, including subclinical and clinical mastitis: clinical mastitis includes mild, severe, and chronic mastitis. See, for example, Iscovich et al., U.S. Pat. No. 7,958,513. In subclinical mastitis, no swelling of the breast or udder can be detected, nor can there be observable abnormalities in the milk. This type of mastitis can be commonly referred to as "hidden." However, special screening tests including, for example, the California Mastitis Test (CMT), the Wisconsin Mastitis Test (WMT) based on an estimation of somatic cell counts (SCC) and the catalase test, can show changes in milk composition and provide an indication of subclinical mastitis. Clinical mastitis can be mild or severe, and acute or (less commonly) chronic mastitis, can be characterized by the presence of leukocytes in the milk along with physical changes in appearance of the milk, cow, or both. Mild clinical mastitis can involve changes in the milk's appearance including presence of flakes or clots, watery milk, or other unusual forms of the milk. Mild clinical mastitis can be accompanied by other symptoms including hot, sensitive or swollen breast or udder. Severe clinical mastitis involves the symptoms of hot, sensitive, firm breast or udder that can be quite painful to the lactating animal. The onset of severe clinical mastitis can often be sudden and the lactating animal may become systemically ill, showing signs of sepsis or toxemia including fever, rapid pulse, depression, weakness and loss of appetite. When the whole lactation system of the animal is affected, the condition can be referred to as acute systemic mastitis. The severe symptoms can also be accompanied by cessation of milk production. Chronic mastitis can be represented as persistent udder infection, typically in the form of subclinical mastitis, which occasionally can develop into the clinical form, and back to the subclinical form. Chronic mastitis can be characterized by hard lump(s) within the mammary gland due to the establishment of bacteria and the formation of connective or scar tissue and occasionally microabcesses.

As used herein, the term "bovine mastitis" refers to a polymicrobial disease characterized by inflammation of the udders of dairy and beef cattle. The infection has huge implications to health and welfare of animals, impacting milk and beef production and costing up to EUR 32 billion (35 BILLION USD) annually to the dairy industry, globally. Bacterial communities associated with the disease include representative species from *Staphylococcus, Streptococcus, Enterococcus, Escherichia, Klebsiella* and a number of other, minor pathogens. Conventional treatment relies on antibiotics, but antimicrobial resistance, declining antibiotic innovations, and biofilm production negatively impact therapeutic efficacy (Nale and McEwan 2023).

As used herein, the term "treatment" or "treating" refers to an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, delaying or slowing the progression of the disease, ameliorating the disease state, and decreasing the dose of one or more other medications required to treat the disease. The methods of the invention contemplate any one or more of these aspects of treatment. Treatment includes "prevention" which means providing prophylaxis with respect to the occurrence or recurrence of a disease in a subject that may be predisposed to the disease but has not yet been diagnosed with the disease.

As used herein, the term "individual" or "subject" refers to an animal, lactating or non-lactating, including, but not limited to, a cow, a goat, a sheep, a buffalo, a camel, a donkey, a llama, a horse, a pig, a human, a primate, a mule, a cat, and a dog. The individual can benefit from bacteriophage therapy for the treatment or prevention of a bacterial infection. In some embodiments, the individual is a human. In some embodiments, the individual is a farm animal, for example, a dairy cow.

As used herein, the term "therapeutic amount" or "effective amount" or similar refers to an amount effective, at dosages and for periods of time necessary, to achieve the desired therapeutic or prophylactic result. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount can be provided in one or more administrations. In the case of treating bacterial infections, an effective amount is an amount of an agent or a composition sufficient to cause an effect on the growth of the bacteria. The effective amount of the antibacterial agent or composition, when used alone or in combination, may: (i) reduce the number of bacterial cells; (ii) inhibit, retard, slow to some extent, and preferably stop bacterial proliferation; (iii) inhibit bacterial growth; (iv) inhibit adhesion of bacterial cells to host cells; (v) inhibit invasion of bacterial cells into the host cells; (vi) inhibit colonization of bacterial cells into host cells or tissues; (vii) prevent or delay occurrence and/or recurrence of bacterial infection; and/or (viii) relieve to some extent one or more of the symptoms associated with the bacterial infection.

As used herein, the term "dry period" can refer to the phase in a dairy animal before parturition in which lactation has ceased. According to present practices in the dairy industry, involution and subsequent cessation of milk production can occur by initiating the dry period, after which time the milk secretion capacity can be restored at the time of parturition.

As used herein, the term "beginning of the dry period" can refer to the dry period, typically about 60 days, in a cow, before an expected parturition.

As used herein, the term "transition period" refers to a period beginning from the last three weeks prior to parturition through the first three weeks following parturition. During this time, a cow can be immunosuppressed and can have increased susceptibility to developing mastitis though symptoms can evade detection.

As used herein, the term "lactating period" is described as milking period.

As used herein, the term "medical cleaner" is defined as a composition that could be used to remove or retard growth of one or more harmful bacteria by its topical application on a living tissue such as, but not limited to, a wound, biofilm formed on skin, etc.

As used herein, the term "waiting time" is defined as a time-period during which no milking is done on a treated animal. Waiting time is often required in antibiotic treatment, so that the antibiotic in the treated animal has been assimilated, and the milk does not contain antibiotic residue or contain residue within acceptable range set by a government regulatory body. In the antibiotic treated animal, such waiting time is about 2 to 3 weeks irrespective of somatic cell counts. That means, during this time, treated animals cannot be milked, leading to economic loss for a farmer.

As used herein, the term "epigenetic modification" refers to chemical alterations to DNA and histone proteins that regulate gene expression without changing the underlying DNA sequence. Epigenetic modification could be due to DNA Methylation, histone modification, non-coding RNA modification, etc., In an embodiment, bacteriophage is epigenetically modified by host encoded methylase.

It should be noted herein that any feature or component described in association with a specific embodiment may be used and implemented with any other embodiment unless clearly indicated otherwise.

Composition

An embodiment of the invention provides compositions comprising one or more bacteriophages or a mutant thereof and a storage solution.

In an embodiment, bacteriophages have grown on specific host bacteria, and so the host-encoded methylases have epigenetically-modified the genomes of these bacteriophages, thus enabling the bacteriophages to overcome the bacterial defense mechanisms.

Exemplary bacteriophages are bacteriophage strain EB1, such as bacteriophage strain EB1.11, deposited under number DSM 34393, bacteriophage strain EB1.25 deposited under number DSM 34394, bacteriophage strain EB1.27 deposited under number 34395. Another exemplary example of bacteriophage includes bacteriophage strain STA1.29 deposited under number DSM 34396 and bacteriophage strain MA2.74 deposited under number DSM 34397, wherein said strains were deposited at German Collection of Microorganisms on Sep. 28, 2022.

In an embodiment, the invention provides a cocktail of bacteriophages to treat mastitis. As used herein, "bacteriophage cocktail" refers to a composition having two or more bacteriophages.

In an embodiment, the cocktail includes a bacteriophage with a podovirus morphology, and another bacteriophage with a myovirus morphology. Exemplary bacteriophages with a podovirus morphology include EB1.11 EB1.25 and EB1.27. Exemplary bacteriophages with a myovirius morphology include STA1.29 and MA2.74.

In an embodiment, of the present invention, a bacteriophage has a podovirus morphology.

In an embodiment, of the present invention a bacteriophage has a myovirus morphology.

In an embodiment, the cocktail includes a bacteriophage selected from genus of Twortlikevirus, and another bacteriophage selected from a member of a genus Ahjdlikevirus.

Exemplary Ahjdlikevirus include EB1.11 EB1.25, EB1.27. Exemplary Twortlikevirus include STA1.29 and MA2.74.

In an embodiment, composition includes at least one bacteriophage selected from EB1.11 EB1.25, EB1.27, STA1.29 and MA2.74. In another embodiment, composition includes a cocktail of at least two bacteriophages, such as EB1.11 and EB1.25; EB1.11 and EB1.27; EB1.11 and STA1.29; EB1.11 and MA2.74; EB1.25 and EB1.27; EB1.25 and STA1.29; EB1.25 and MA2.74; EB1.27 and STA1.29; EB1.27 and MA2.74; MA2.74 and STA1.29. In another embodiment, composition includes a cocktail of at least 3 bacteriophages, such as EB1.11, EB1.25 and EB1.27; EB1.11, EB1.25 and STA1.29; EB1.11, EB1.25 and MA2.74; EB1.11, EB1.17 and STA1.29; EB1.11, EB1.17 and MA2.74; EB1.11, STA1.29 and MA2.74; EB1.17, EB1.25 and STA1.29; EB1.17, EB1.25 and MA2.74; EB1.25, STA1.29 and MA2.74; EB1.27, STA1.29 and MA2.74. In another embodiment, the composition includes combinations of at least four bacteriophages, such as EB1.11, EB1.25, EB1.27 and STA1.29; EB1.11, EB1.25, EB1.27 and MA2.74; EB1.11, EB1.25, STA1.29 and MA2.74; EB1.11, EB1.27, STA1.29 and MA2.74; EB1.25, EB1.27, STA1.29 and MA2.74. In an embodiment, the composition contains a cocktail of at least five bacteriophages, such as EB1.11, EB1.25, EB1.27, STA1.29 and MA2.74

In an embodiment, one or more bacteriophages from EB1.11, EB1.25, EB1.27, STA1.29 and MA2.74 have a broad range of activity against relevant *Staphylococcus aureus* strains. In some embodiments, one or more bacteriophages from EB1.11, EB1.25, EB1.27, STA1.29 and MA2.74 have a broad range of activity against relevant *Staphylococcus aureus* strains and in combination they cover 90% of a panel of strains associated with mastitis. In some embodiments, they cover about 80, 85% 90%, 95%, 99% or more of a panel of strains associated with mastitis.

In an embodiment, one or more bacteriophages from EB1.11, EB1.25, EB1.27, STA1.29 and MA2.74 have a broad range of activity against relevant *Staphylococcus aureus* strains. In some embodiments, one or more bacteriophages from EB1.11, EB1.25, EB1.27, STA1.29 and MA2.74 have a broad range of activity against relevant *Staphylococcus aureus* strains and in combination they cover 90% of a panel of strains associated with bovine mastitis. In some embodiments, they cover about 80, 85% 90%, 95%, 99% or more of a panel of associated *Staphylococcus aureus* strains with bovine mastitis. In an embodiment, cocktail of bacteriophages has activity against on one or more drug resistant *Staphylococcus aureus*, such as but not limited to methicillin-resistant *Staphylococcus aureus*.

In an embodiment, the composition has a mutant of one or more bacteriophages selected from EB1.11, EB1.25, EB1.27, STA1.29 and MA2.74.

In an embodiment, one or more bacteriophages from EB1.11, EB1.25, EB1.27, STA1.29 and MA2.74 target a Gram-positive bacterium. The Gram-positive bacterium is selected from the group comprising *Staphylococcus aureus*.

State of the art buffers to stabilize bacteriophage products contain phosphate (e.g., PBS) or TRIS(HCl) (e.g., SM buffer). Neither buffer system is suitable for an intra-mammary application. Phosphate buffers will lead to the precipitation of $Ca_3(PO_4)_2$ and thus to precipitates in raw milk. Tris(hydroxymethyl)aminomethane-based buffers are not food grade and thus not suitable for in vivo applications.

In an embodiment, the composition provides a storage solution. As used herein, the term "storage solution" is a vehicle system for a composition having one or more bacteriophages so that the composition has a shelf-life and is suitable for direct in vivo application. In an embodiment, 'direct in vivo application' may include dilution of the composition.

The storage solution is an isotonic storage solution.

Isotonic storage solution is a sterile, colorless clear liquid. The isotonic storage solution contains 0.9% NaCl with magnesium and/or calcium salt. In another embodiment, isotonic solution contains a higher concentration of magnesium salt compared to calcium salt. Higher concentration may be about 20 times, 15 times, 10 times, 9 times, 8 times, 7 times, 6 times, 5 times, 3 times, 2 times more than calcium salt.

In an embodiment, magnesium salt includes magnesium chloride, or magnesium sulphate, etc.

In an embodiment, calcium salt includes calcium chloride, or calcium sulphate, etc.

In an embodiment, the isotonic storage solution contains 0.9% NaCl, 10 mM $MgCl_2$ and 1 mM $CaCl_2$.

In an embodiment, the isotonic storage solution solves at least a threefold purpose. First, the solution stabilizes a cocktail of bacteriophages selected from bacteriophages shown in Table 1. Cocktail may include 2, 3, 4, or all 5 bacteriophages (Table 1). Second, the solution must be food grade. Third, the solution must be freely miscible with raw milk, thus allowing the injection of the bacteriophage cocktail via the teat channel into the udder of a lactating cow, or another lactating animal, to cure mastitis caused by *Staphylococcus aureus*.

In an embodiment, the composition containing isotonic storage solution avoids coagulation of the raw milk in bovine udders and teats, when applied via injection into the teat channel.

In an embodiment, less than 10%, 9%, 8%, 5%, 3%, 1%, or less amount of the raw milk gets coagulated in mammals, such as in bovine udders and teats.

In an embodiment, the composition does not contain a phosphate buffer.

In an embodiment, the composition does not contain a TRIS buffer.

In an embodiment, the raw milk in mammals does not coagulate with use of this composition.

In an embodiment, the composition also comprises a plant extract having a bactericidal or bacteriostatic property. By "bacteriostatic" means the inhibition of growth or replication or proliferation or reproduction of the targeted bacterium. "Bactericidal" is meant as the killing of bacteria. For convenience, bacteriostatic and bactericidal will be referred to as "anti-bacterial" unless otherwise indicated. Without any limitation, such plants could be selected from the genus *Aegopodium, Salicornia, Chenopodium, Cydonia, Origanum, Sorbus, Ribes, Cichorium, Cistus, Geum, Hippophaë, Sideritis, Cicer* and *Prunus* as described in US20140322324. Other plant species could be *Alnus pendula* as described in U.S. Pat. No. 8,399,033; *Eremophila longifolia* as described in US20120189558, *Satureja gilliesii* as described in WO2016/106463; *P. silvestris* as described in US20100111994, *Curcumin Longa*, etc. Extract could be prepared by any known process suitable as per understanding of a person skilled in the art.

In an embodiment, the composition includes one or more pharmaceutical excipients to form a pharmaceutical composition.

The term "pharmaceutically acceptable excipient" is defined as substances other than the active pharmaceutical ingredient that have been appropriately evaluated for safety and are intentionally included in a drug delivery system which facilitates processing of the drug formulation during its manufacture; protect, support, and/or enhance stability, bioavailability, or patient acceptability; facilitate in the effectiveness and/or delivery of the drug formulation and assist in maintaining the integrity of the drug formulation during its storage across its shelf life. Pharmaceutically acceptable excipients are well known, and one skilled in pharmaceutical art can easily select an excipient suitable for particular routes of administration (Remington's Pharmaceutical Sciences, Mack Publishing Co., Easton, Pa., 1985). A pharmaceutically acceptable excipient could be lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil, but not always limited thereto. The pharmaceutical composition of the present invention can additionally include lubricants, wetting agents, sweetening agents, flavors, emulsifying agents, suspending agents, and adjuvants, in addition to the above ingredients.

The pharmaceutical composition of the present invention can be formulated by using a pharmaceutically acceptable carrier and/or excipient according to a method generally performed by those in the art as a unit dose or in a multi-dose container. At this time, the formulation can be oil or a solution in aqueous media, suspension or emulsion, extract, powder, granule, tablet or capsule, and a dispersing agent or a stabilizer can be additionally included therein.

Method of Treatment

In some embodiments, there is provided a method of treating or preventing a disease caused by a bacterial infection in an individual or a subject comprising administering a therapeutic amount of the composition as described herein to the individual. In one embodiment, the disease includes mastitis. In some embodiments, the mastitis is subclinical mastitis. In some embodiments, mastitis is chronic mastitis. In some embodiments, the mastitis is septic mastitis.

In an embodiment, one or more compositions could be administered to a subject or via parenteral administration exemplified by intravenous administration, intraperitoneal administration, intramuscular administration, hypodermic administration, or local administration. In some embodiments, the composition is suitable for oral administration. In some embodiments, the composition is suitable for topical application. In some embodiments, the delivery vehicle is an ointment. In some embodiments, the composition is suitable for intra mammary via the teat channel. In some embodiments, composition is suitable for infusion, injection, or application to the mammary gland, including but not limited to the teat, the teat opening, into the teat streak canal, or teat sinus.

In some embodiments, the composition is administered intramammarily. In some embodiments, the individual is subsequently administered a teat sealant. In some embodiments, the composition is administered during a lactating period. In some embodiments, the composition is administered during a dry period. In some embodiments, the composition is administered at the beginning of the dry period at cessation of milking. In some embodiments, the composition is administered during a transition period.

In an embodiment, composition may be packaged into standard medical syringes (5 to 10 mL) under sterile conditions. Filled syringes are individually packaged in a heat-sealed plastic wrap. On site, e.g., in a cow shed, the veterinarian would unwrap the syringe and fit the nozzle with a protective tip (separately packaged). This protective tip is then carefully inserted into the teat channel of the animal, passing the constrictor muscle of the teat, allowing the veterinarian to inject the composition into the teat channel. By manually massaging the teat, the composition is then distributed higher up into the udder.

In an embodiment, the composition should be administered to a bovine at least once daily. In another embodiment, the composition could be administered multiple times in a day such as: 2 times, 3 times, 4 times or more.

In an embodiment, the composition could be administered after milking of the bovine. In another embodiment, the composition could be administered after milking the bovine.

In an embodiment, composition as described herein is applied after the regular milking of the animal. As cows are milked every 12 hours, a single application could have a therapeutic effect for about 12 hours. With the next milking, the bacteriophage solution will be removed from the udder as a component of the milk. As a single application might not be sufficient to remove/kill/attack all *Staphylococcus aureus* germs (may be located in biofilms) causing the mastitis, a treatment regime of six injections over a period of three days is recommended.

In an embodiment, treatment regime of six to ten to twenty injections over a period of about 3 to 5 to 10 days or more is also possible. For example, in the case of animals with recurring infections, a longer treatment regime of six to twenty injections over a period of about 3 to 10 days may be suitable.

In an embodiment, 1 mL of the injected composition has the potency of about $1\times10^8$ PFU/mL to about $10^{10}$ PFU/mL per liter of milk produced in an individual quarter of the udder during twelve hours. In another embodiment, the 1 mL of the composition has a potency of about $1\times10^9$ PFU/mL. For example, a cow that produces 40 L of milk per day would produce 5 L of milk in a single quarter in 12 hours. Accordingly, 5 mL of bacteriophage product should be injected into a mastitis affected quarter. During the 12 hours, the bacteriophage product will be diluted with freshly produced milk. Shortly before the next milking, the concentration will reach $1\times10^6$ PFU/mL of milk. This is a therapeutically active concentration as shown in, for example, Tietze et al. 2020, leading to a reduction of the *Staphylococcus aureus* count in milk.

In some embodiments, the composition treats the mastitis by reducing the activity, function, and/or amount of the host bacteria by amount 20%, 50%, 70%, 90% or more. In yet another embodiment, the composition has the ability to cause an overall decrease of activity, function, and/or amount of the host bacteria by about 75%, 85%, 90%, 95%, 99% or greater.

Advantages

In an embodiment, the composition is substantially freely miscible with raw milk. By term, "substantially freely miscible", inventor means that the composition forms a homogenous solution without precipitation or separation or curdling of components of milk. In short, the composition does not lead to phase separation in the raw milk. Due to the freely miscible nature of the composition with raw milk, injection of the composition via the teat channel into the udder of a lactating cow or another lactating animal is possible.

In an embodiment, the composition could be used as a medical cleaner.

In an embodiment, the composition is stable for at least about a year at 39.2-46.4° F. The terms "stability" and "shelf life" could be interchangeably used. It refers to the length of time that a commodity may be stored without becoming unfit for use, consumption, or sale. In an embodiment, during storage period, bacteriophage concentration in the composition either remains substantially the same or decreases less than 45%, 40%, 35%, 30%, 25%, 20%, 10%, 5% or less. In an embodiment, bacteriophage concentration in the composition is less than 0.5 log reduction, such as less than 0.4 log reduction, 0.3 log reduction, 0.2 log reduction, 0.1 log reduction or less.

In an embodiment, during storage period, there is substantially no change in the bacteriophage concentration. In an embodiment, the bacteriophage concentration decreases by about 25% or less during storage period. The time-period of storage is about 6 months, 1 year, 1.5 year, 2 years, 3 years or more.

In an embodiment, storage solution could also be used as an application solution and/or injectable material to bovine for treatment.

In an embodiment, the composition has a potency of about $1 \times 10^7$ PFU/mL to about $10^{10}$ PFU/mL (PFU/mL=plaque forming units per milliliter of solution, equivalent to active bacteriophage particles per milliliter of solution). In an embodiment, the composition has a potency of about $10^6$ PFU/mL, $10^7$ PFU/mL, $10^8$ PFU/mL, $10^9$ PFU/mL, $10^{10}$ PFU/mL, $10^{11}$ PFU/mL, $10^{12}$ PFU/mL, $10^{13}$ PFU/mL, $10^{14}$ PFU/mL or more. In an embodiment, potency refers to potency of each bacteriophage present in the composition. In some embodiments, the potency refers to cumulative effect of all bacteriophages present in the composition.

In an embodiment, potency of the composition remains substantially the same during storage period. In some embodiments, potency of the composition may decrease slightly by about 10 to 20% during storage period.

In an embodiment, treatment of disease by the composition of the present invention has no waiting time. The composition of the present invention allows a treatment in a bovine animal without waiting period, so the milk could be harvested immediately after application. In some cases, a treated cow could be milked from the moment the somatic cells have come within normal range. In some embodiments, waiting time may be very small such as 1 day or 2 days after the cow has been treated and the somatic cells have come within normal range.

To date, no bacteriophage product, with a broad efficacy, stabilized in a food grade storage solution, suitable for in vivo applications, has been described. The composition described herein has a broad efficacy, stabilizing in a food grade storage solution and suitable for in vivo applications.

In an embodiment, present invention reduces use of antibiotics in the food chain, avoiding all negative impacts of creating antibiotic resistance in livestock. Economic benefits for the farmer (no waiting time and no loss of milk); and there is no re-emergence of the pathogen, which is often observed when mastitis is treated with antibiotics.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Bacteriophage having activity against *Staphylococcus aureus* Wild type *Staphylococcus aureus* strains often carry defense mechanisms, such as restriction/modification systems, that render them less susceptible to bacteriophage infection. The bacteriophages of the invention have been grown on specific host bacteria, and so the host-encoded methylases have epigenetically-modified the genomes of these bacteriophages, thus enabling the bacteriophages to overcome the bacterial defense mechanisms.

Two step fermentation for the bacteriophage components, which are blended with the isotonic storage solution, filled sterile into ready to use syringes, which are then used to inject the composition into the teat channel of a lactating cow or another lactating animal suffering from mastitis. Table 1 provides details of bacteriophage and respective host bacterium.

TABLE 1

| Bacteriophages and host strain | |
|---|---|
| Phage with DSMZ deposit number | Host strains with DSMZ deposit number |
| EB1.11 (DSM 34393) | *Staphylococcus aureus* ST11 (DSM 34387) |
| EB1.25 (DSM 34394) | *Staphylococcus aureus* ST25 (DSM 34388) |
| EB1.27 (DSM 34395) | *Staphylococcus aureus* ST27 (DSM 34389) |
| STA1.29 (DSM 34396) | *Staphylococcus aureus* ST29 (DSM 34390) |
| MA2.74 (DSM 34397) | *Staphylococcus aureus* ST74 (DSM 34391) |

TABLE 2

Coverage of a panel of *Staphylococcus aureus* strains by the bacteriophage cocktail disclosed in this invention.

| Cocktail component Strain | EB1.11 DSM 34393 | EB1.25 DSM 34394 | EB1.27 DSM 34395 | STA1.29 DSM 34396 | MA2.74 DSM 34397 | Cocktail |
|---|---|---|---|---|---|---|
| *Staphylococcus aureus* 09-01714 | +++ | ++ | ++ | ++ | +++ | covered |
| *Staphylococcus aureus* 819 | +++ | ++ | | | +++ | covered |
| *Staphylococcus aureus* 820 | | ++ | +++ | | ++ | covered |
| *Staphylococcus aureus* 821 | + | | ++ | ++ | +++ | covered |
| *Staphylococcus aureus* 822 | ++ | ++ | ++ | ++ | +++ | covered |
| *Staphylococcus aureus* 823 | +++ | ++ | +++ | ++ | +++ | covered |
| *Staphylococcus aureus* 824 | + | ++ | +++ | ++ | | covered |
| *Staphylococcus aureus* 825 | + | +++ | | | | covered |
| *Staphylococcus aureus* 826 | + | +++ | + | | | covered |
| *Staphylococcus aureus* 827 | ++ | ++ | ++ | ++ | +++ | covered |
| *Staphylococcus aureus* 828 | ++ | ++ | +++ | +++ | +++ | covered |
| *Staphylococcus aureus* M-1 | | | | ++ | +++ | covered |
| *Staphylococcus aureus* M-2 | ++ | ++ | +++ | +++ | +++ | covered |
| *Staphylococcus aureus* M-3 | | | | | +++ | covered |
| *Staphylococcus aureus* M-4 | + | + | +++ | +++ | +++ | covered |
| *Staphylococcus aureus* M-5 | ++ | ++ | ++ | ++ | +++ | covered |
| *Staphylococcus aureus* M-6 | + | +++ | + | | | covered |
| *Staphylococcus aureus* M-7 | | ++ | ++ | ++ | +++ | covered |
| *Staphylococcus aureus* M-8 | +++ | ++ | +++ | +++ | +++ | covered |
| *Staphylococcus aureus* M-9 | | | | | | not covered |
| *Staphylococcus aureus* M-10 | + | | ++ | ++ | +++ | covered |
| *Staphylococcus aureus* M-11 | +++ | ++ | ++ | ++ | +++ | covered |
| *Staphylococcus aureus* M-12 | +++ | +++ | +++ | ++ | +++ | covered |
| *Staphylococcus aureus* M-13 | | ++ | | | | covered |
| *Staphylococcus aureus* M-14 | +++ | +++ | +++ | ++ | +++ | covered |
| *Staphylococcus aureus* M-15 | ++ | +++ | ++ | ++ | +++ | covered |
| *Staphylococcus aureus* M-16 | ++ | +++ | ++ | | +++ | covered |
| *Staphylococcus aureus* M-17 | ++ | +++ | ++ | | +++ | covered |
| *Staphylococcus aureus* M-18 | | | | ++ | +++ | Covered |
| *Staphylococcus aureus* M-19 | + | | | ++ | +++ | Covered |
| *Staphylococcus aureus* M-20 | + | +++ | | | | Covered |
| *Staphylococcus aureus* M-25 | | | | +++ | +++ | Covered |
| *Staphylococcus aureus* M-29 | + | | + | | | Covered |
| *Staphylococcus aureus* M-30 | +++ | +++ | +++ | ++ | +++ | Covered |
| *Staphylococcus aureus* M-38 | | | | + | + | Covered |
| *Staphylococcus aureus* 132102 | + | + | ++ | ++ | +++ | Covered |

TABLE 2-continued

Coverage of a panel of *Staphylococcus aureus* strains by the bacteriophage cocktail disclosed in this invention.

| Cocktail component Strain | EB1.11 DSM 34393 | EB1.25 DSM 34394 | EB1.27 DSM 34395 | STA1.29 DSM 34396 | MA2.74 DSM 34397 | Cocktail |
|---|---|---|---|---|---|---|
| *Staphylococcus aureus* 9996 | | | | | +++ | Covered |
| *Staphylococcus aureus* 10048 | | | | | +++ | Covered |
| *Staphylococcus aureus* 10154 | | | | ++ | +++ | Covered |
| *Staphylococcus aureus* 10172 | + | +++ | | | | Covered |
| *Staphylococcus aureus* 10201 | | | | ++ | +++ | Covered |
| *Staphylococcus aureus* 5208/13 | + | ++ | ++ | ++ | +++ | Covered |
| *Staphylococcus aureus* 5209/13 | + | ++ | ++ | | +++ | Covered |
| *Staphylococcus aureus* 5214/13 | ++ | ++ | ++ | ++ | +++ | Covered |
| *Staphylococcus aureus* 5219/13 | + | +++ | | | | Covered |
| *Staphylococcus aureus* 5220/13 | + | ++ | | | | Covered |

+++ EOP between 1E+10 and 1E+08
++ EOP between 1E+08 and 1E+06
+ EOP below 1E+06

Figure 1:
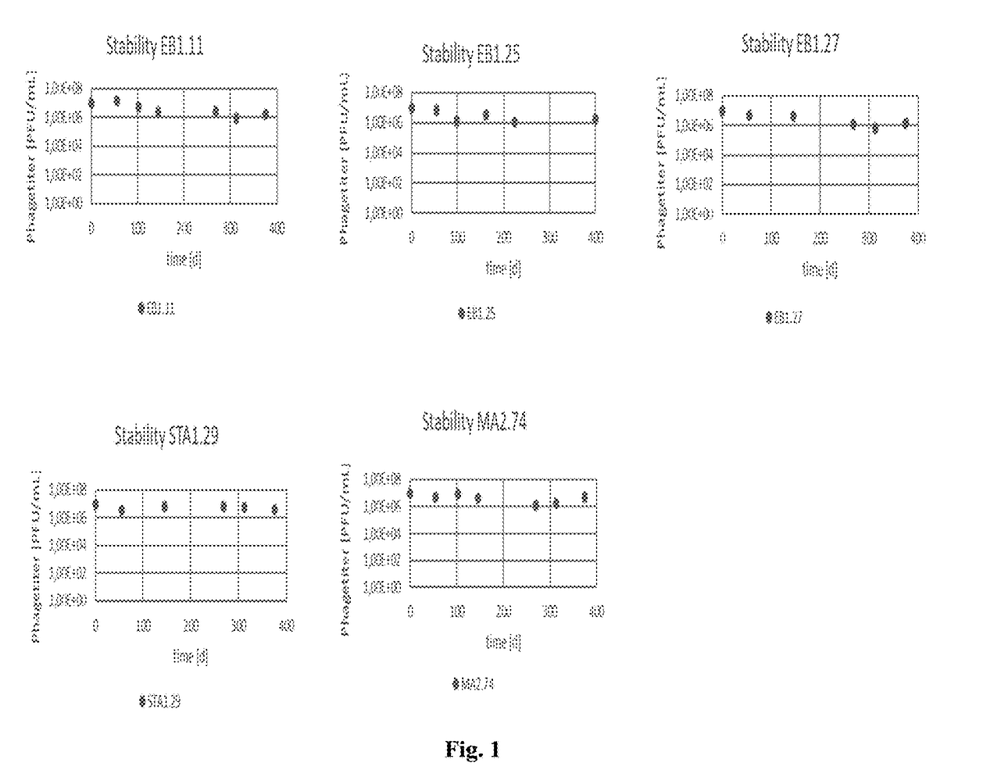
FIG. 1 shows stability of the component bacteriophages in isotonic storage solution. Small fluctuations in the bacteriophage titer are within the error margins of the assay. The graphs show that the five bacteriophages are stable for over a year when stored in the isotonic storage solution described in this invention.

Stability of the composition in isotonic solution is shown in FIG. 1.

Figure 2:
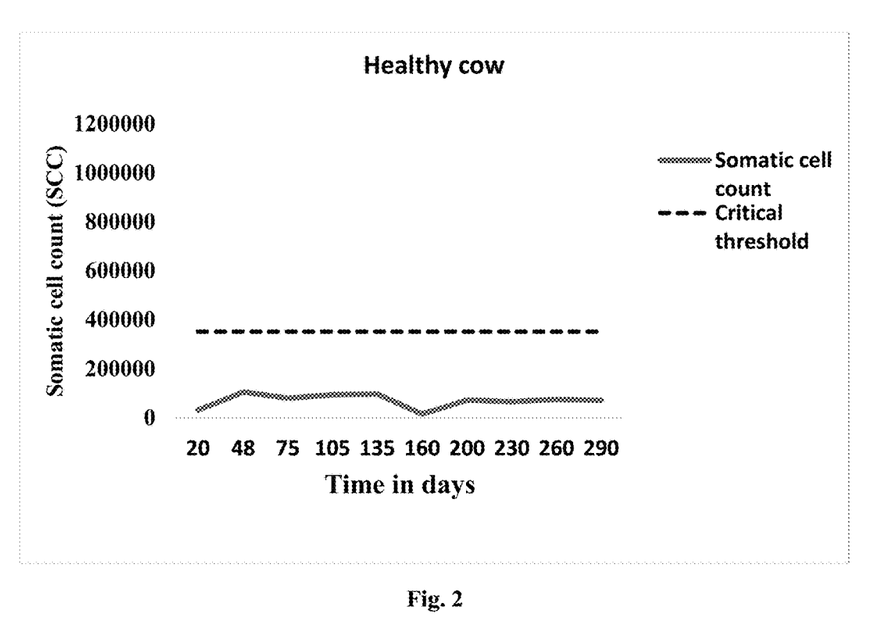
FIG. 2 shows somatic cell count in healthy cow and a critical threshold of somatic cell count in a cow when infected with mastitis.

Example 2: Treatment of the Mastitis in Cow Using the Composition of the Invention A healthy cow during the entire lactation period has a somatic cell count in the range of 100.000 cells per mL of milk. If a cow develops mastitis, the somatic cell count increases. If this somatic cell count rises above a critical threshold of 350.000 cell per mL, the milk will no longer be accepted by a dairy, as shown in FIG. 2.

A cow, which was diagnosed with mastitis caused by *Staphylococcus aureus*, was first unsuccessfully treated with antibiotics. Treatment with the bacteriophage solution described in this invention led to a successful reduction of the somatic cell count and the curing of the cow, as shown in FIG. 3.

Figure 3:
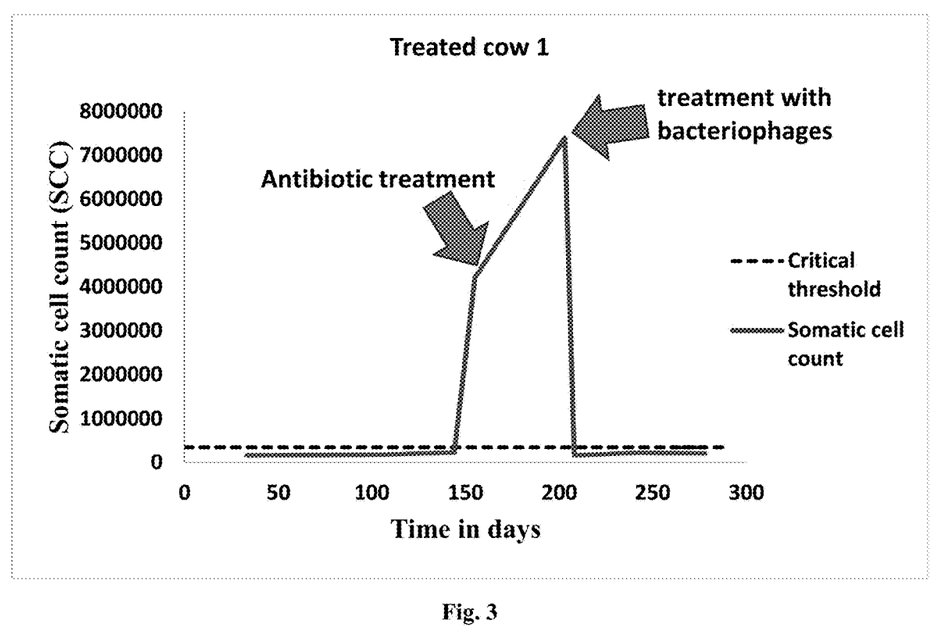
FIG. 3 shows treatment of first cow.
Figure 4:
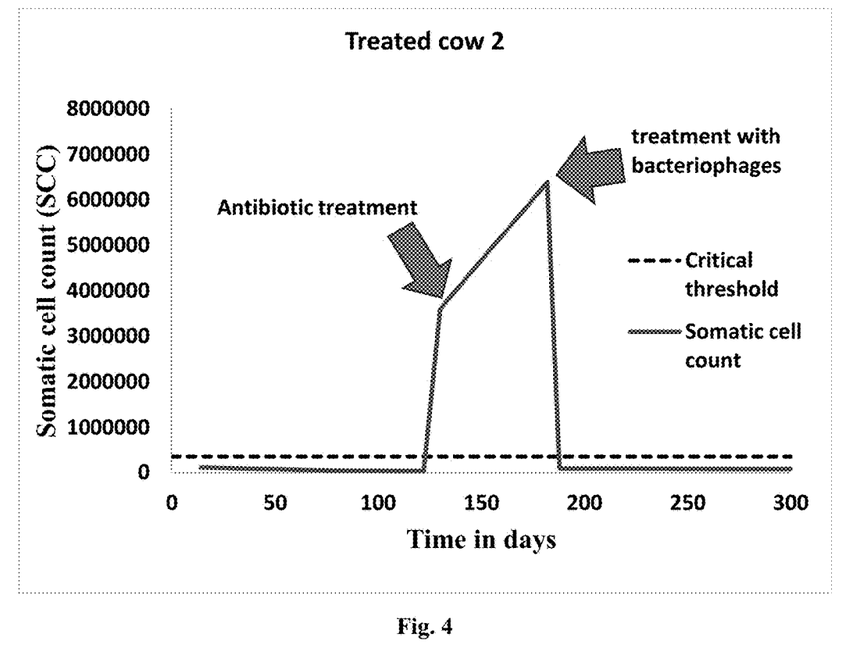
FIG. 4 shows treatment of second cow.

Similar to the situation in FIG. 3, a cow, which was diagnosed with mastitis caused by *Staphylococcus aureus*, was first unsuccessfully treated with antibiotics. A treatment with the bacteriophage solution described in this invention led to a successful reduction of the somatic cell count and the curing of the cow, as described in FIG. 4.

Figure 5:
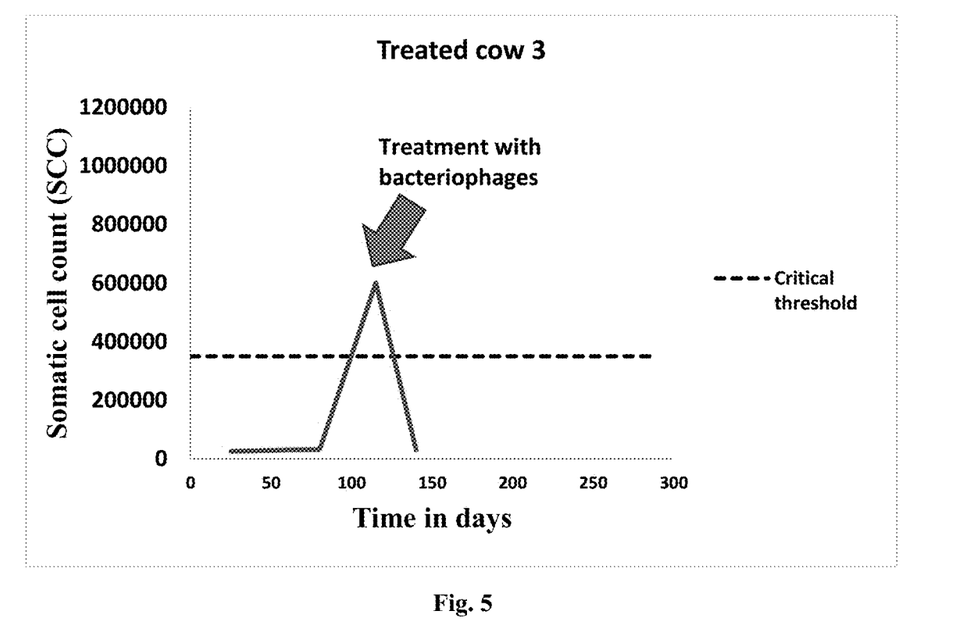
FIG. 5 shows treatment of third cow.

As shown in FIG. 5, a cow, which was diagnosed with mastitis caused by *Staphylococcus aureus*, was immediately treated with the bacteriophage solution described in this invention, without antibiotic treatment. The treatment was successful as seen by the reduction of the somatic cell count.

Figure 6:
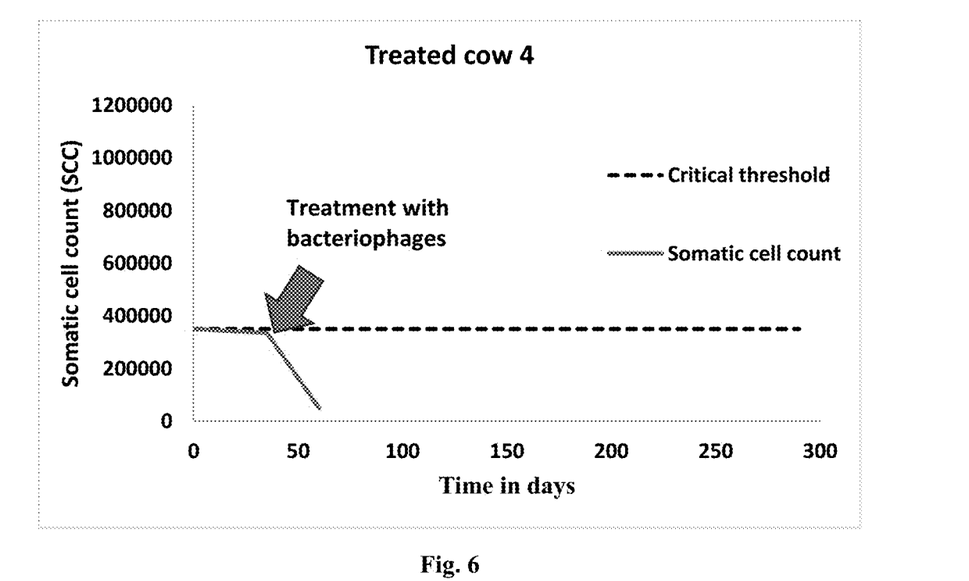
FIG. 6 shows treatment of fourth cow.
Figure 7:
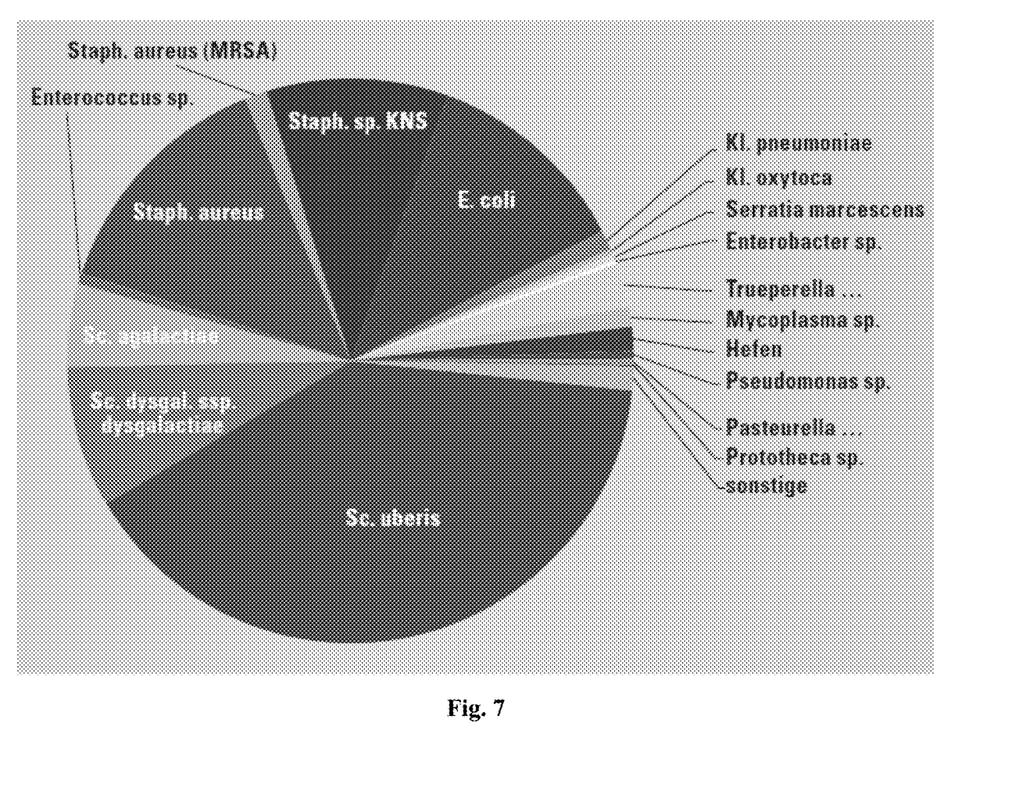
FIG. 7 shows a pie chart of microbes causing mastitis.

As shown in FIG. 6, a cow, showing only subclinical symptoms of mastitis caused by *Staphylococcus aureus*, was immediately treated with the bacteriophage solution described in this invention. The treatment was successful as seen by the reduction of the somatic cell count.

REFERENCES

All references, including granted patents and patent application publications, referred herein are incorporated herein by reference in their entirety.

Gill, J. J., J. C. Pacan, M. E. Carson, K. E. Leslie, M. W. Griffiths, and P. M. Sabour. 2006. "Efficacy and Pharmacokinetics of Bacteriophage Therapy in Treatment of Subclinical *Staphylococcus aureus* Mastitis in Lactating Dairy Cattle." Antimicrobial Agents and Chemotherapy 50 (9): 2912.

Manrique, Pilar, Michael Dills, and Mark J. Young. 2017. "The Human Gut Phage Community and Its Implications for Health and Disease." Viruses 9 (6): 9-11.

Nale, Janet Y., and Neil R. McEwan. 2023. "Bacteriophage Therapy to Control Bovine Mastitis: A Review." Antibiotics 12 (8): 1-21.

Ngassam-Tchamba, C., J. N. Duprez, M. Fergestad, A. De Visscher, T. L'Abee-Lund, S. De Vliegher, Y. Wasteson, et al. 2020. "In Vitro and in Vivo Assessment of Phage Therapy against *Staphylococcus aureus* Causing Bovine Mastitis." Journal of Global Antimicrobial Resistance 22: 762-70.

O'Flaherty, S., R. P. Ross, J. Flynn, W. J. Meaney, G. F. Fitzgerald, and Aidan Coffey. 2005. "Isolation and Characterization of Two Anti-Staphylococcal Bacteriophages Specific for Pathogenic *Staphylococcus aureus* Associated with Bovine Infections." Letters in Applied Microbiology 41 (6): 482-86.

Titze, Isabel, Tatiana Lehnherr, Hansjörg Lehnherr, and Volker Krömker. 2020. "Efficacy of Bacteriophages against *Staphylococcus aureus* Isolates from Bovine Mastitis." Pharmaceuticals 13(3).

U.S. Pat. No. 8,377,431B2
U.S. Ser. No. 11/311,582B2
US20190307818A1

What is claimed is:
1. A composition, comprising:
    (a) a bacteriophage or a mutant thereof selected from a group consisting of bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 343962 and bacteriophage strain MA2.74 deposited under number DSM 34397, wherein said strains were deposited at German Collection of Microorganisms on Sep. 28, 20221; and (b) a storage solution comprising a sodium salt, a calcium salt and a magnesium salt, wherein the magnesium salt is at least 5 times more than the calcium salt;

wherein the bacteriophage or the mutant thereof is capable of killing a Gram-positive bacterium comprising Staphylococcus aureus;

wherein the composition does not contain a TRIS buffer or a phosphate buffer;

wherein the composition is stable for at least about a year at 39.2-46.4° F. (4-8° C.); and wherein the composition avoids coagulation of raw milk.

2. The composition of claim 1, wherein the composition is substantially freely miscible with raw milk.

3. The composition of claim 1, wherein the composition comprises at least two bacteriophages or mutants thereof selected from the group consisting of EB1.11, EB1.25, EB1.27, MA2.74 and STA1.29.

4. The composition of claim 3, wherein a first bacteriophage has a podovirus morphology, and a second bacteriophage has a myovirus morphology, wherein the first bacteriophage is selected from bacteriophage strain EB1.11, EB1.25 and EB1.27, and wherein the second bacteriophage is selected from bacteriophage strain STA1.29 and MA2.74.

5. The composition of claim 1, wherein the composition comprises at least three bacteriophages or mutants thereof selected from the group consisting of EB1.11, EB1.25, EB1.27, MA2.74 and STA1.29.

6. The composition of claim 5, wherein a cocktail of three bacteriophages having combination of bacteriophages having a podovirus morphology and myovirus morphology, wherein a podovirus morphology bacteriophage is selected from bacteriophage strain EB1.11, EB1.25 and EB1.27, and wherein a myovirus morphology bacteriophage is selected from bacteriophage strain STA1.29 and MA2.74.

7. The composition of claim 1, wherein the composition comprises at least four bacteriophages or mutants thereof selected from the group consisting of EB1.11, EB1.25, EB1.27, MA2.74 and STA1.29.

8. The composition of claim 7, wherein bacteriophages or mutants thereof comprise EB1.11, EB1.25, EB1.27, MA2.74 and STA1.29.

9. The composition of claim 7, wherein the composition is configured to treat mastitis in a mammal.

10. The composition of claim 9, wherein the composition is configured to treat bovine mastitis.

11. The composition of claim 9, wherein the composition is configured to be administered to the mammal in a dosage range between about $1 \times 10^7$ to about $1 \times 10^{10}$ PFU/ml of each phage at least once daily.

12. The composition of claim 7, wherein the composition is configured to have no waiting time after a somatic cell count is within a normal range varying from about 70,000 cells per mL to about 250,000 cells per mL of milk.

13. The composition of claim 7, wherein the composition further contains a plant extract having anti-bacterial property.

14. The composition of claim 7, wherein pH of the composition is about 6 to 8.

15. The composition of claim 7, wherein the composition has a potency of about $1 \times 10^7$ PFU/mL to about $10^{10}$ PFU/mL.

16. The composition of claim 15, wherein a concentration of a bacteriophage in the composition reduces less than 0.5 log during a storage period of about 3 years at a temperature about 4° C. to 8° C.

17. A kit, comprising: a composition, comprising:
(a) a bacteriophage or a mutant thereof selected from a group consisting of bacteriophage strain EB1.11 deposited under number DSM 34393, bacteriophage strain EB1.25 deposited under number DSM 34394, bacteriophage strain EB1.27 deposited under number 34395, bacteriophage strain STA1.29 deposited under number DSM 34396 and bacteriophage strain MA2.74 deposited under number DSM 34397, wherein said strains were deposited at German Collection of Microorganisms on Sep. 28, 2022;

wherein the bacteriophage or the mutant thereof is capable of killing a Gram-positive bacterium comprising Staphylococcus aureus; and (b) a dilutant to dilute the composition, comprising: a solution comprising a sodium salt, a calcium salt and a magnesium salt, wherein the magnesium salt is at least 5 times more than the calcium salt;

wherein the composition: (i) is stable for at least about a year at 39.2-46.4° F. (4-8° C.), and (ii) does not contain a TRIS buffer or a phosphate buffer.

18. The kit of claim 17, wherein pH of the composition is about 6 to 8.

19. The kit of claim 17, wherein the composition has a potency of about $1 \times 10^7$ PFU/mL to about $10^{10}$ PFU/mL.

20. The kit of claim 17, wherein the composition is configured to avoid coagulation of raw milk and is miscible with the raw milk.

* * * * *